(12) United States Patent
Goldenberg et al.

(10) Patent No.: US 6,353,774 B1
(45) Date of Patent: Mar. 5, 2002

(54) HIGH PRECISION VISION GUIDED POSITIONING DEVICE

(75) Inventors: Andrew A. Goldenberg, Toronto; Nenad Kircanski, North York; Sasan Raghibizadeh, Toronto, all of (CA)

(73) Assignee: Virtek Engineering Sciences Inc., Waterloo (CA)

( * ) Notice: Subject to any disclaimer, the term of this patent is extended or adjusted under 35 U.S.C. 154(b) by 0 days.

(21) Appl. No.: 09/667,670

(22) Filed: Sep. 22, 2000

(51) Int. Cl.[7] .............................................. G06F 19/00
(52) U.S. Cl. ......................... 700/245; 29/431; 29/701; 382/145; 382/190; 382/287; 382/291; 382/294; 209/584
(58) Field of Search ........................... 700/245, 29/431, 29/701, 703, 771, 822; 209/584; 118/256; 382/287, 291, 154, 190, 294; 356/623

(56) References Cited

U.S. PATENT DOCUMENTS

| | | | | |
|---|---|---|---|---|
| 4,821,408 A | * | 4/1989 | Speller, Sr. et al. | 29/701 |
| 5,220,718 A | * | 6/1993 | Speller, Sr. et al. | 29/431 |
| 5,506,682 A | * | 4/1996 | Pryor | 356/623 |
| 5,653,005 A | * | 8/1997 | Speller, Sr. et al. | 29/701 |
| 5,939,022 A | * | 8/1999 | Franciskovich | 422/100 |
| 6,201,203 B1 | * | 3/2001 | Tiles | 209/584 |
| 2001/0009136 A1 | * | 7/2001 | Bryning et al. | 1118/256 |
| 2001/0018216 A1 | * | 8/2001 | Kowallis | 436/44 |

OTHER PUBLICATIONS

Yang et al., H(sub infinity) Control design for positioning performance of gantry robots, 2000, IEEE, pp. 3038–3042.*
Majors et al., Time–optimal transportation of flexible payloads, 1997, IEEE, pp. 3455–3460.*
Oh, Visual servoing by partitioning degrees of freedom, 2001, IEEE, pp. 1–17.*
Bisiach et al., The adaptation of gantry–robot, operating in a Railway Industry Co., 1998, IEEE, pp. 2132–2136.*

* cited by examiner

Primary Examiner—William A. Cuchlinski, Jr.
Assistant Examiner—McDieunel Marc
(74) Attorney, Agent, or Firm—Nancy E. Hill; Hill & Schumacher

(57) ABSTRACT

A positioning device includes a gantry robot and an elevator unit. The gantry robot includes a head assembly, a work-space spaced below the head assembly for receiving at least one tray and a device for moving the head assembly in the X, Y and Z directions. The gantry robot further includes a device for scanning the work-space. The elevator unit has a plurality of shelves arranged in a series one above another. Each shelf is adapted to receive at least one tray and the shelves are movable in the Z direction. A device for moving a tray between the elevator unit and the work-space is included. A control system for controlling the movement of the head assembly in the X, Y and Z direction, for controlling the movement of the shelves in the Z direction and for controlling the tray moving device is operably connected to the gantry robot and the elevator unit.

19 Claims, 13 Drawing Sheets

HIGH PRECISION VISION GUIDED POSITIONING DEVICE

FIELD OF THE INVENTION

This invention relates to high precision positioning devices and in particular to positioning devices for use in the automatic detection, manipulation, repositioning and super positioning of biological samples.

BACKGROUND OF THE INVENTION

The use of a positioning device for colony picking and gridding is known. Typically these devices include a picker head and a platform or working area. The picker head and the platform are movable relative to each other in the X, Y and Z directions, where the X and Y directions are orthogonal axes on the platform and Z is normal to the platform. In some devices the platform moves in the X direction and the picker head moves in the Y and Z directions while in other devices the picker head moves in all three directions and the platforms are stationary. Many of the devices also include a stacker such that a plurality of plates may be stacked. However, the capacity of each device is limited by the footprint of the device.

Accordingly it would be advantageous to provide a device that increases the capacity without increasing the footprint of the device. Further it would be advantageous to provide a device that is modular, reconfigurable and multi-functional.

SUMMARY OF THE INVENTION

A positioning device includes a gantry robot and an elevator unit. The gantry robot includes a head assembly, a work-space spaced below the head assembly for receiving at least one tray and a device for moving the head assembly in the X, Y and Z directions. The gantry robot further includes a device for scanning the work-space. The elevator unit has a plurality of shelves arranged in a series one above another. Each shelf is adapted to receive at least one tray and the shelves are movable in the Z direction. A device for moving a tray between the elevator unit and the work-space is included. A control system for controlling the movement of the head assembly in the X, Y and Z direction, for controlling the movement of the shelves in the Z direction and for controlling the tray moving device is operably connected to the gantry robot and the elevator unit.

The device includes a packing/unpacking system that allows for automatic packing or unpacking of several microwell plates (or other similar labware) into or from reusable packages. Each package is used to transfer and process multiple plates (one batch of plates may contain eight or more plates) simultaneously. Each package or batch is labeled and identified by a bar-code label. Such an identification number allows for systematic storing, tracking, and retrieval of all the information related to that batch.

The device includes a controlled environment for storing the trays on the elevator unit when not in use. A tray is a plate that has precisely defined size and that contains labware (a predetermined number of microwell plates, Petri plates, membranes, etc.). The bottom part of the elevator unit is an enclosed and insulated environment, with a controlled temperature and humidity. Each time the device completes the operations related to the current trays on the platforms, the trays are loaded to the available bottom shelves of the elevator. Then, the elevator will move the two shelves down into the refrigerated enclosure.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Figure 1:
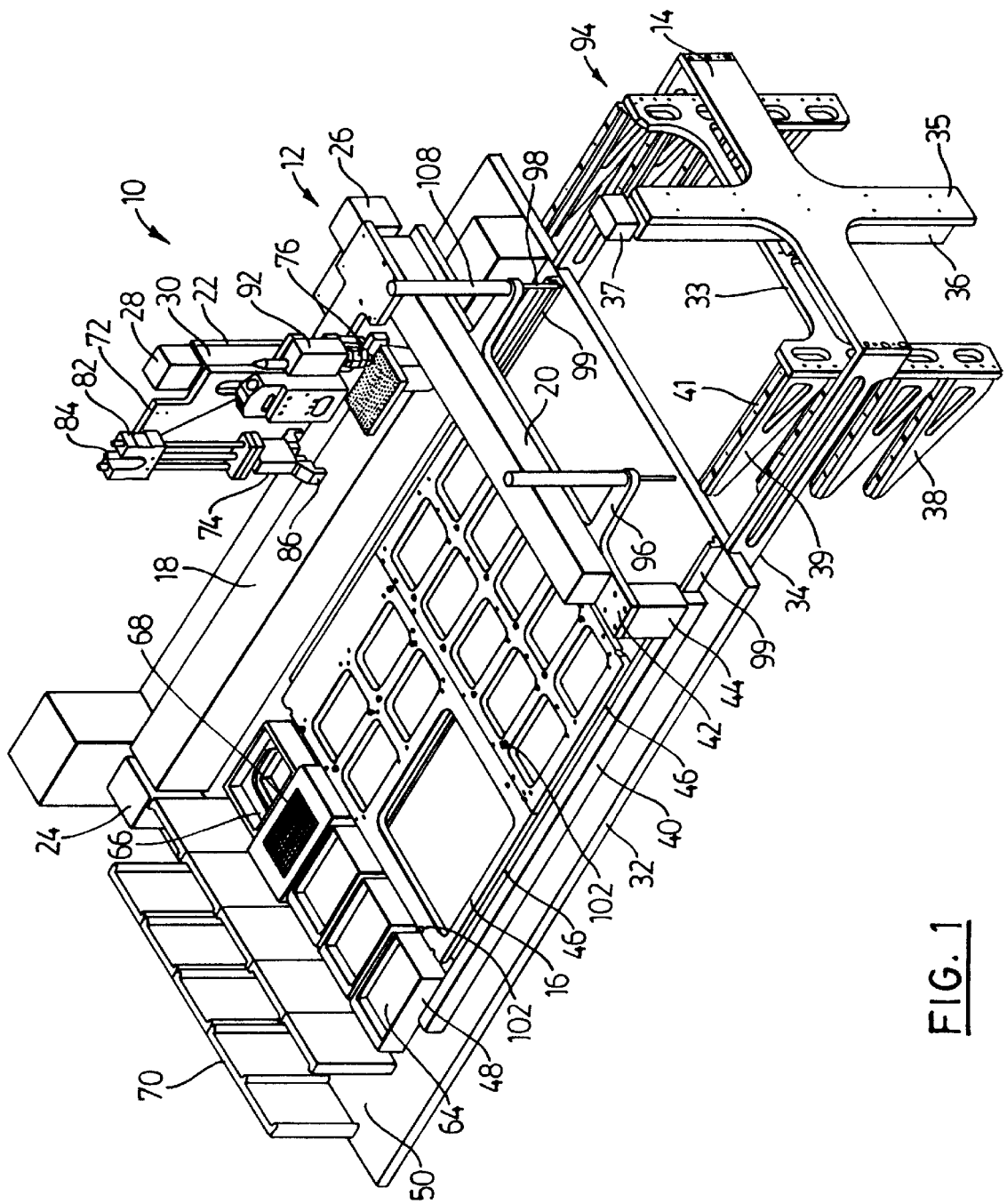
FIG. 1 is a perspective view of the high precision vision guided positioning device constructed in accordance with the present invention.

Referring to FIG. 1, the high precision vision guided positioning device of the present invention (hereinafter referred to as the positioning device) is shown generally at 10. The positioning device 10 includes a gantry robot 12 and an elevator unit 14. The positioning device 10 is a modular, reconfigurable, and multi-functional robot designed for automatic picking/arraying/re-arraying/gridding/and microarraying of bacteria, yeast, or phage colonies or other biological samples. Picking refers to collecting randomly distributed samples from Petri plates and transferring the samples to microwell plates or other labware. Arraying refers to collecting the samples from microwell or gel plates and transferring the samples onto gel plates in an orderly fashion such as a matrix of spots or samples. Re-arraying refers to picking up selected individual colonies, and re-positioning them in a pre-defined order. Gridding refers to collecting the samples form microwell plates and transferring the samples onto membranes. Microarraying refers to collecting the samples from the microwell plates and transferring the samples onto glass slides.

Gantry robot 12 has 3-degrees-of-freedom (3-dof) and elevator unit 14 has 1-degree of freedom (dof). The gantry robot 12 provides a means for performing predetermined or programmed tasks within the work-space of the machine and the elevator unit 14 is used for storing and loading a plurality of holding plates called trays 16. Each tray 16 can hold/carry different number and type of labware.

Gantry robot 12 consists of an X linear actuator 18, a Y linear actuator 20 and a Z linear actuator 22. Each linear actuator is driven by a separate motor 24, 26 and 28 respectively. Each motor provides linear motion for the head assembly 30 along its respective axis. A main plate 32 is the structural base for the gantry robot 12. The X linear actuator and the Y linear actuator define the work-space.

Figure 11:
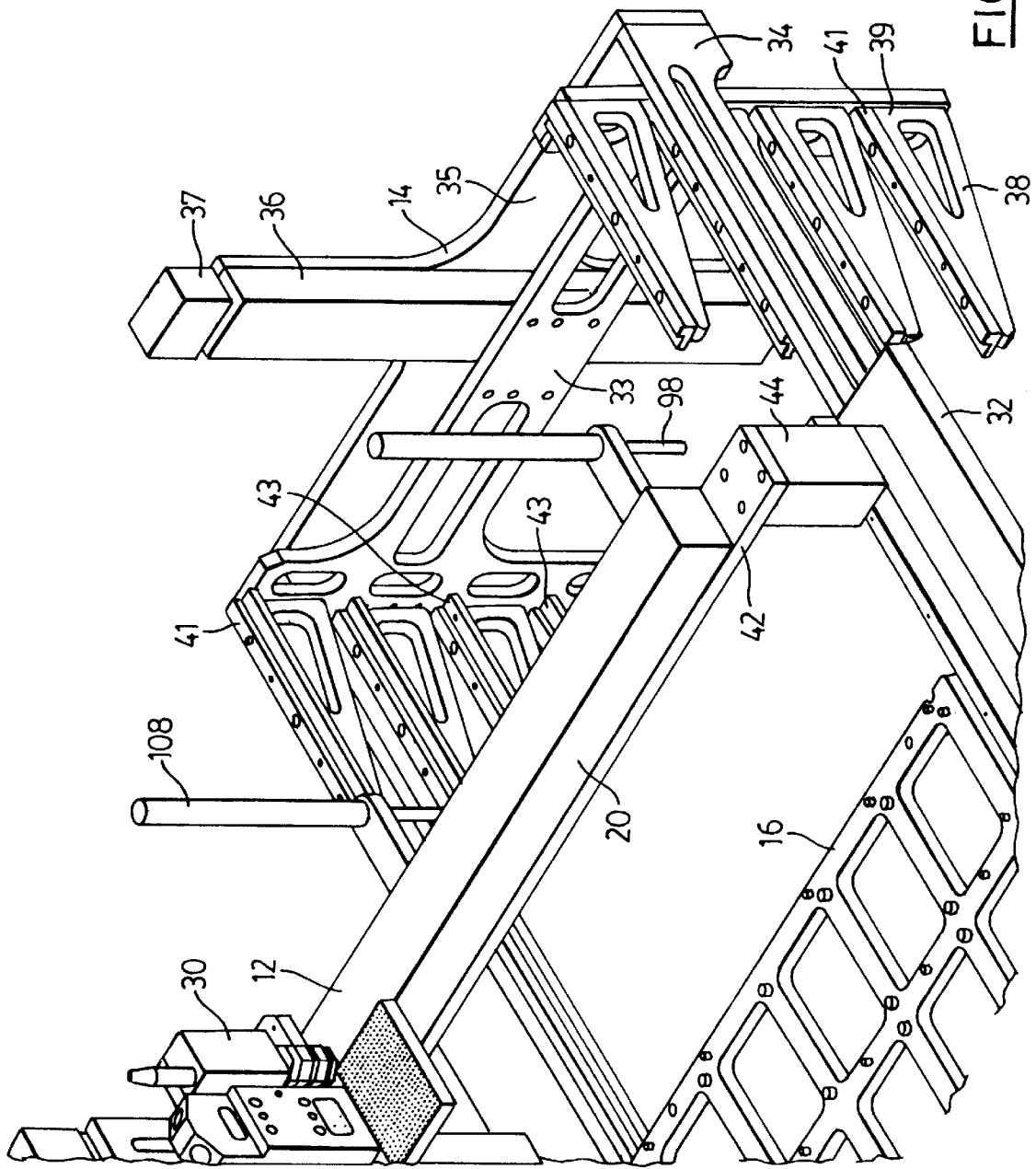
FIG. 11 is an enlarged perspective view of the elevator unit of the positioning device of the present invention.
Figure 12:
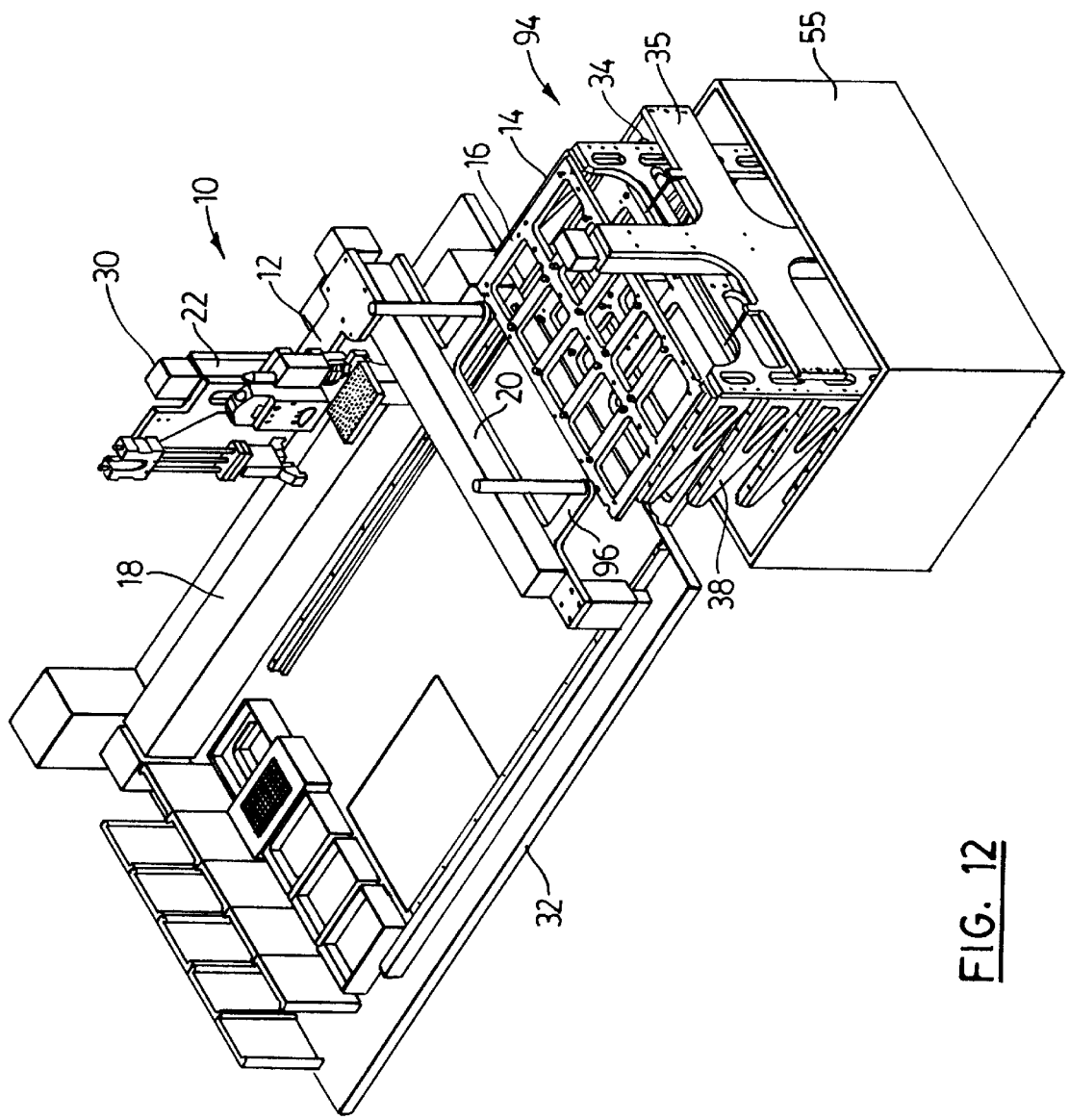
FIG. 12 is a perspective view of the positioning device of the present invention showing the elevator unit including a refrigerator enclosure.

Elevator unit 14 is attached to main plate 32 with two side supports 34. A back support 35 is attached between the two supports 34. The elevator unit 14 is outside of but adjacent to the work-space. Side supports 34 and back support 35 are stationary. An elevator linear actuator 36 is attached to the back support 35. An elevator motor 37 is attached to linear actuator 36 and together they provide the up/down motion of a plurality of shelves 38, shown here by way of example as four shelves. Each shelf 38 includes a pair of side portions 39 connected to a common back portion 33. Each side portion 39 has an L-shaped support 41 attached thereto. The L-shaped support 41 provides a ledge adapted to receive a tray 16. Stoppers 43, best seen in FIG. 11, are positioned at the back of some of the shelves such that lower trays 16 extend inwardly from upper trays. The stoppers 43 are arranged such that the lower trays or groups of lower trays extend inwardly from the upper trays to provide access to the tray loader 94. Where the main plate 32 is dimensioned to receive two trays then the stoppers 43 are arranged such that the position of groups of two trays are the same. The elevator unit 14 may include a refrigerator enclosure 55 as shown in FIG. 12.

Figure 13:
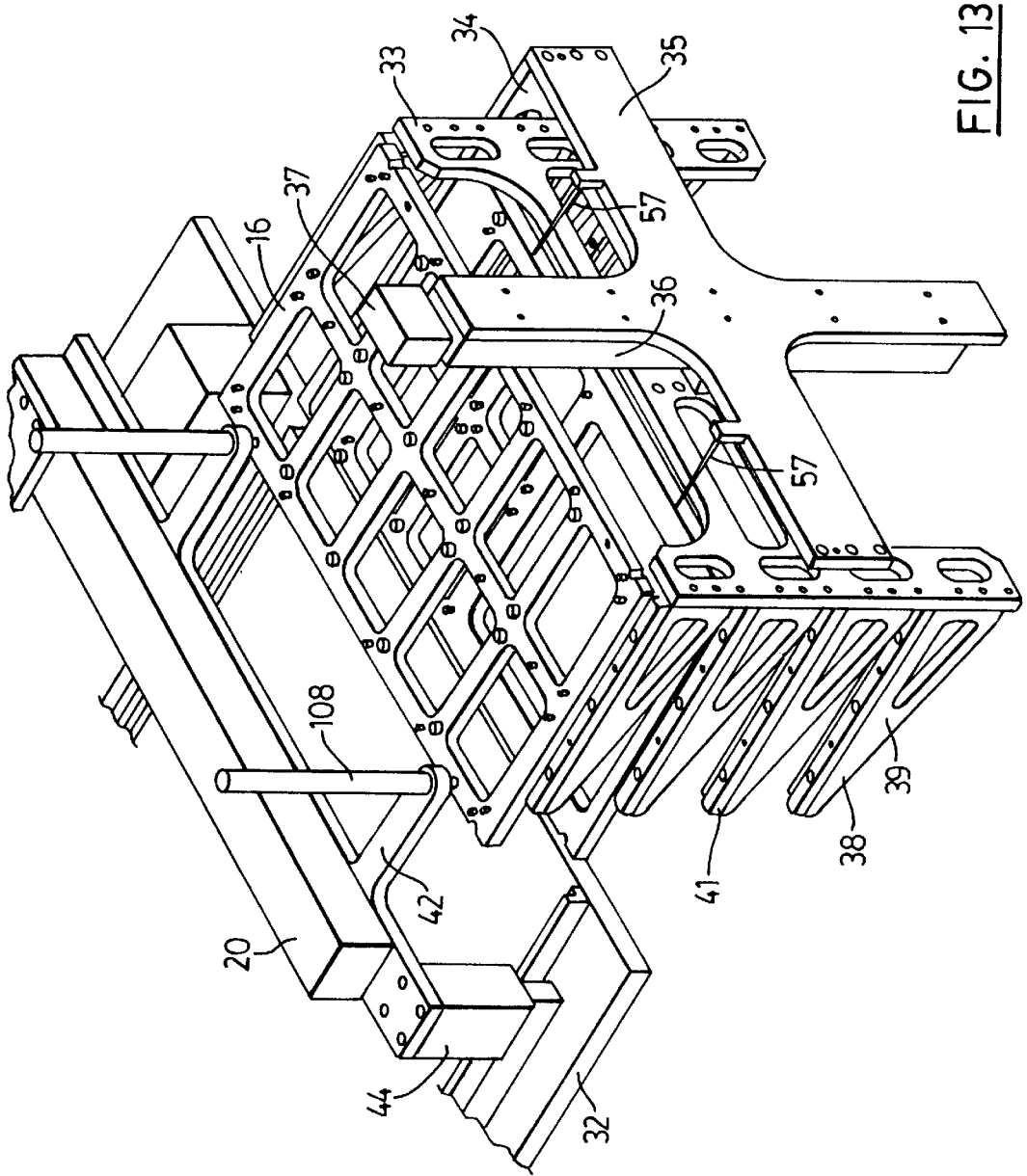
FIG. 13 is an enlarged perspective view an alternate embodiment of the elevator unit of the positioning device of the present invention.
Figure 14:
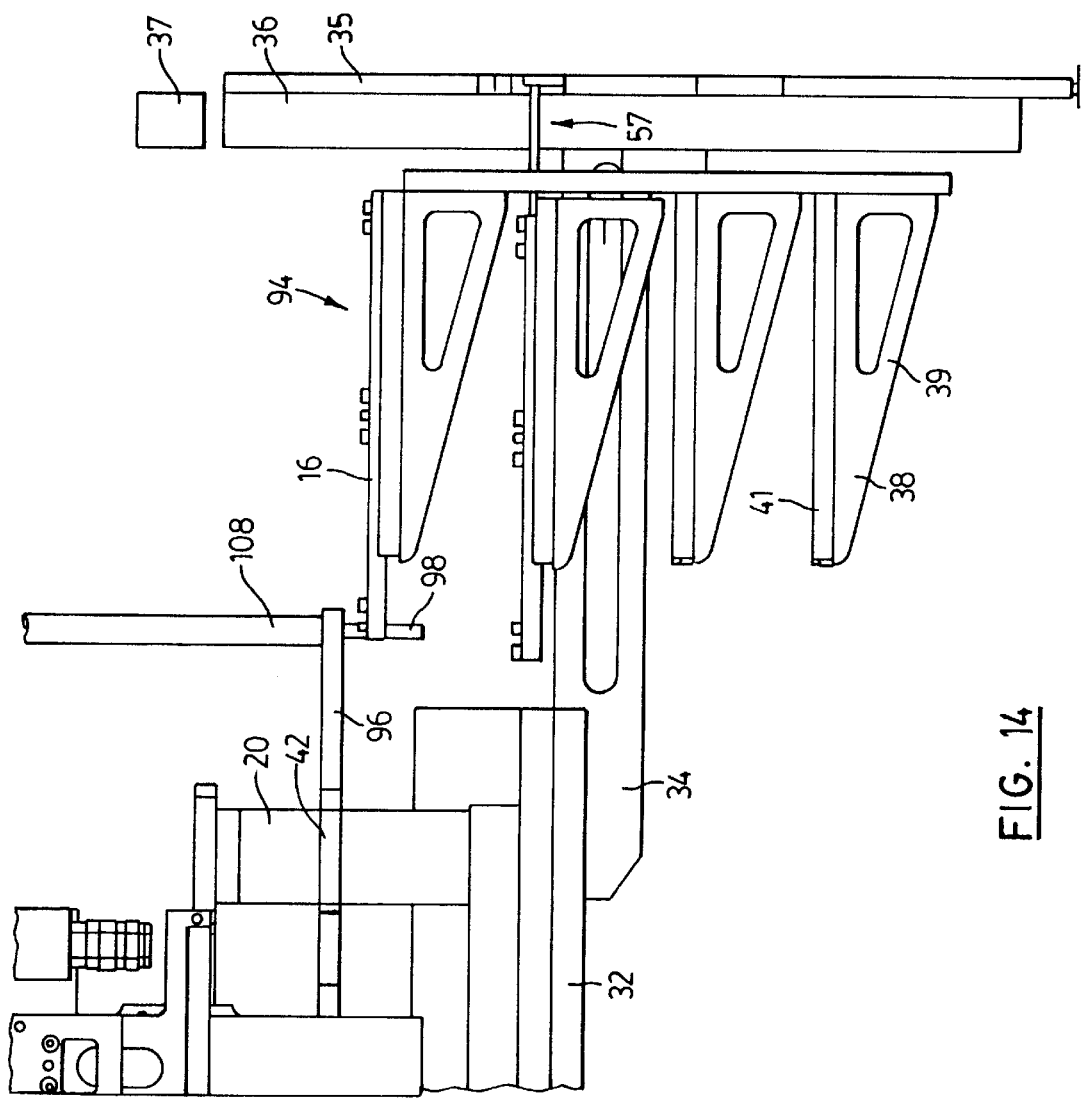
FIG. 14 is an enlarged side view of the elevator unit shown in FIG. 13.

Alternatively an elevator X linear actuator 57 may be used to push a tray inwardly toward the tray loader 94, as shown in FIGS. 13 and 14. The tray need only pushed inwardly enough to provide access to hole or depression 102 in tray 16. The elevator X linear actuator 57 is aligned with a tray 16 when it is pushed onto platform 46. The elevator X linear actuator is attached to back support 35.

To move the head assembly 30 in the X axis there is an X motor 24, and X linear actuator 18 and a rail 40 parallel to the X linear actuator 18. The X linear actuator 18 and the rail 40 are spaced apart and are attached to the main plate 32.

The Y linear actuator 20 is attached to a connecting plate 42 which extends between the X linear actuator 18 and the rail 40. A spacer 44 raises up connecting plate 42 so that it is level. Y motor 26 moves head assembly 30 along the Y axis.

Z motor 28 and Z linear actuator 22 move the head assembly 30 up and down or along the Z axis.

Main plate 32 is divided into a plurality of areas. The number and function of the areas can be adapted by the user. In the embodiment shown in FIGS. 1 and 2, main plate 32 has two platforms 46, a cleaning area 48 and a stacking area 50.

Figure 5:
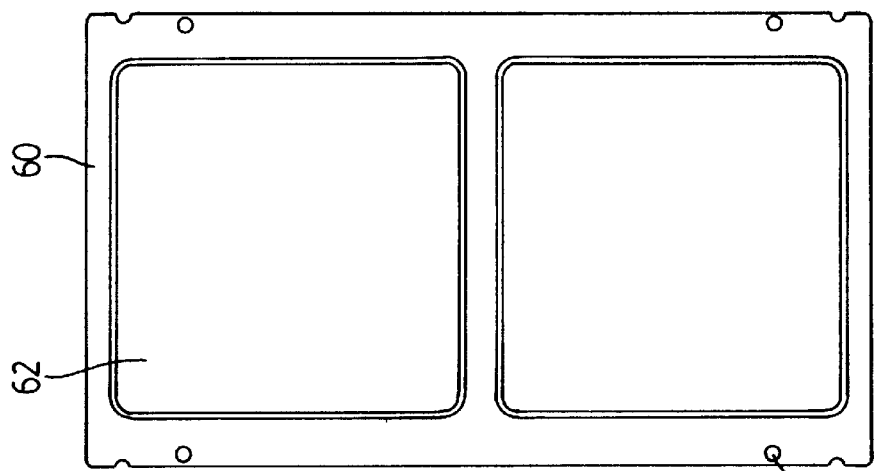
FIG. 5 is a top view of a membrane tray for use in association with the positioning device of the present invention.
Figure 4:
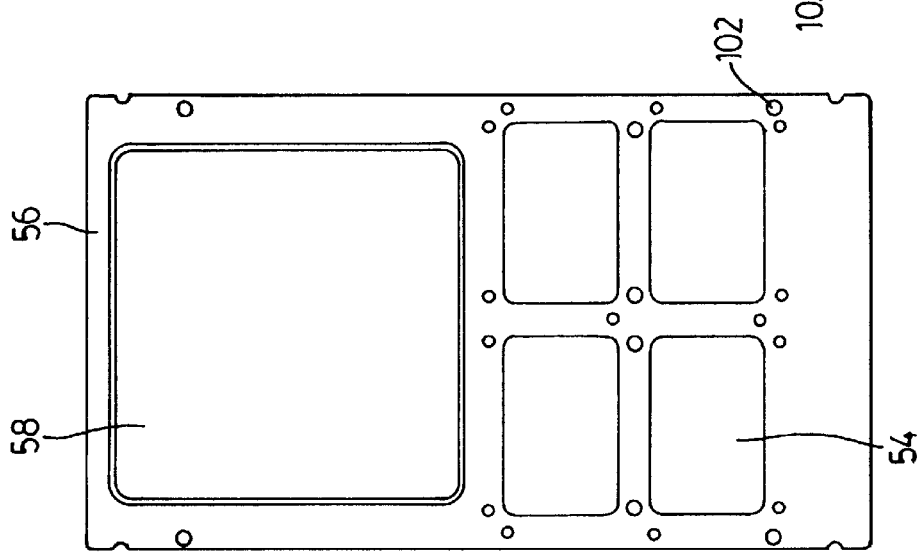
FIG. 4 is a top view of a Petri plate tray for use in association with the positioning device of the present invention.
Figure 3:
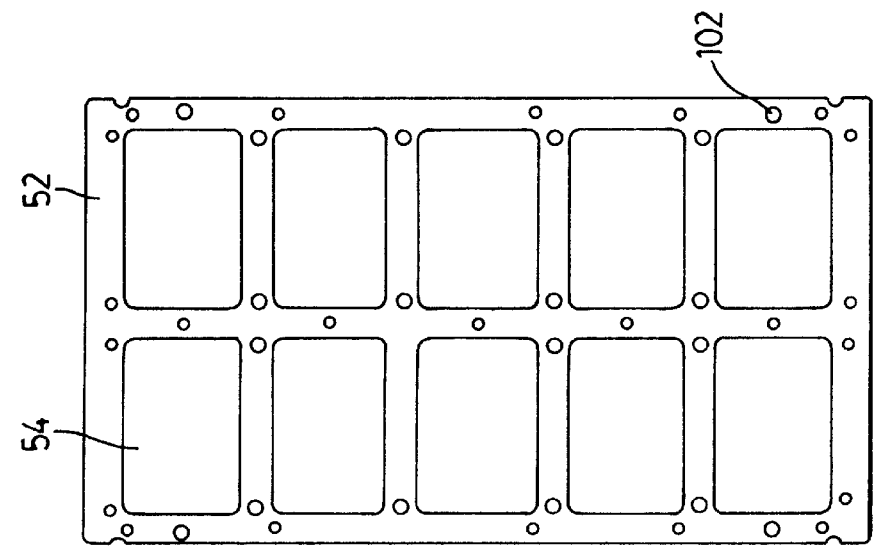
FIG. 3 is a top view of a microwell tray for use in association with the positioning device of the present invention.

Each platform 46 is dimensioned to hold one tray 16. Since a tray has precisely defined dimensions, or the same footprint, any tray can be brought to the platform by sliding from right to left or removed from the platform by sliding from left to right along the X direction. A pair of rails 99 are positioned on the platform 46 for receiving trays 16. The gantry robot 12 performs the sliding (storing and retrieving) of the trays to and from the elevator unit 14. The pair of rods 98 move along the X axis with the robot and thus can transfer a tray to and from the elevator by sliding. The rods are actuated so that the rods can engage or release from the matching holes 102 in the trays. There is a wide range of configurations that can be used for each tray. Three examples of trays 16 are shown in FIGS. 3 to 5. All trays 16 have the same external footprint (X and Y dimensions). However, different trays 16 are designed to hold different types of labware. A microwell plate holder tray 52 is shown in FIG. 3. Tray 52 is designed to hold up to 10 standard size microwell plates 54, or other labware of a similar footprint. Tray 52 can be used for colony picking, colony arraying, liquid handling, re-arraying, gridding, and micro-arraying applications. Alternatively a Petri plate holder tray 56 is shown in FIG. 4. Tray 56 holds one large size Petri plate 58 (or omni-tray), and four standard microwell plates 54. Tray 56 is typically used for colony-picking applications. Another alternative is shown in FIG. 5 and is a membrane holder tray 60. Tray 60 holds two large-size membranes 62, or two large-size omni-trays. Tray 60 can be used for gridding applications. As can be seen from these examples the variety of tray types can be designed to hold special labware or other items for variety of applications as long as the trays have the predetermined foot print. Accordingly using different designs of trays, provides means for modularity, reconfigurability, and multi-functionality of positioning device 10.

Preferably the cleaning area 48 includes a washing station 64, a drying station 66 and a sonicator 68. Preferably at least two types of wash stations are used, namely an automatic washing station, and a regular wash station. Automatic washing station is attached to fill and drain pumps for automatic filling and emptying of the container. Up to three washing stations 64 can be mounted in the cleaning area 48. Each washing station can contain different type of wash solution. The designs of washing stations are modular, such that they can be easily removed from the main plate 32 and replaced by other modules such as a microwell or tip-rack holders. The drying station 66 generates a uniform flow of hot air for fast drying of the pins after washing. A sonicator or ultrasonic cleaner is mounted on the main plate 32 for better removal of residuals on the pins. The elements of the cleaning area 48 are used for cleaning, sterilizing, and drying of pins and can be adapted because of the modularity to different types and sizes of pins that are utilized for different applications. For example the cleaning area can be used for pins used for replicating, gridding, arraying, re-arraying, and picking of bacteria colonies.

Figure 2:
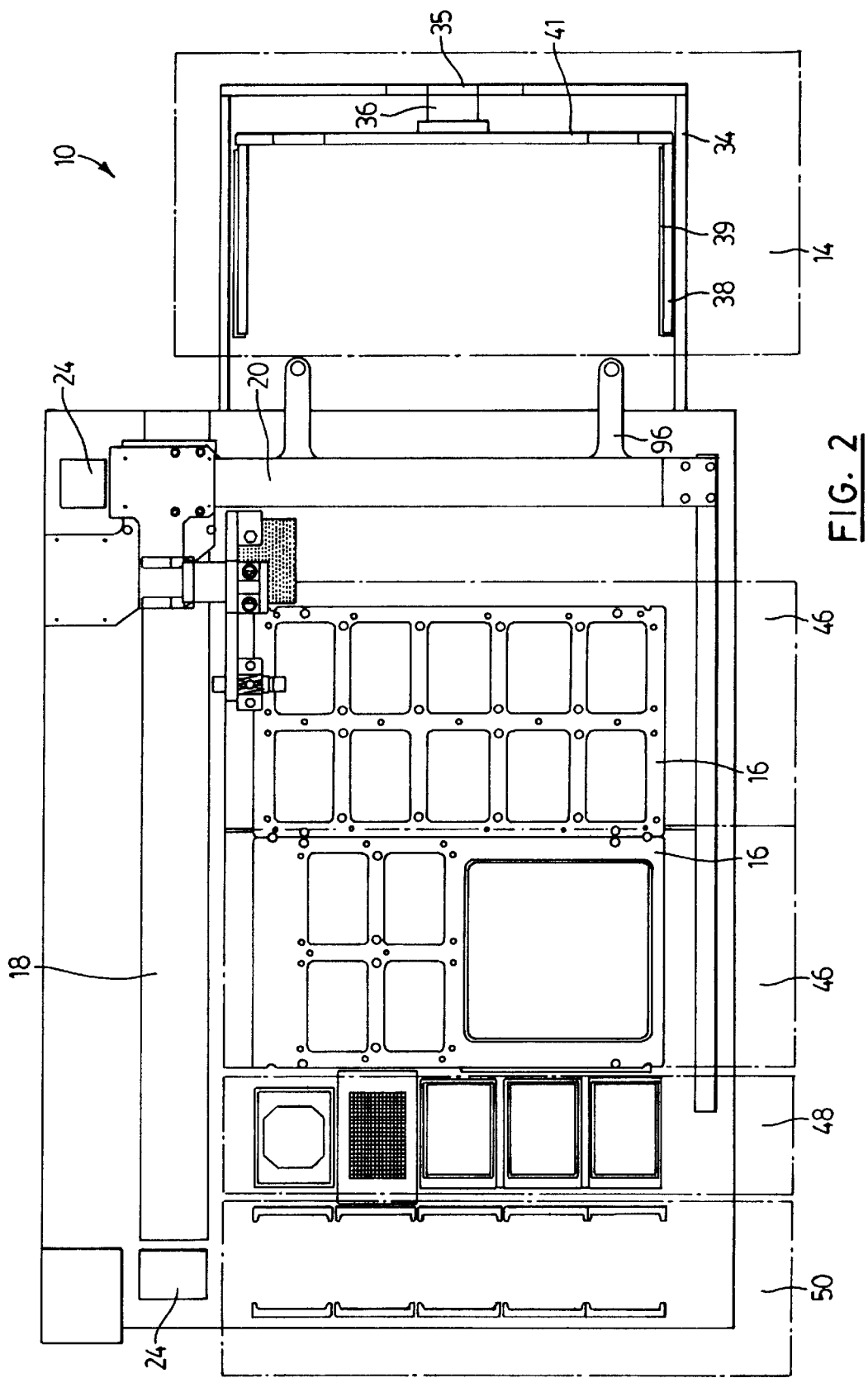
FIG. 2 is a top view of the positioning device of the present invention.

The stacking area 50 has a plurality of stackers 70. FIGS. 1 and 2 show five stackers 70. Each stacker 70 is used for temporary storage of a plurality of plates 54. Preferably at least eight plates 54 can be stacked in each stacker 70. Reusable packages can be mounted on the stacking area for automatic packing and unpacking of several plates. Plates that are packed in a reusable package can be easily transferred to other places for subsequent processing.

Figure 9:
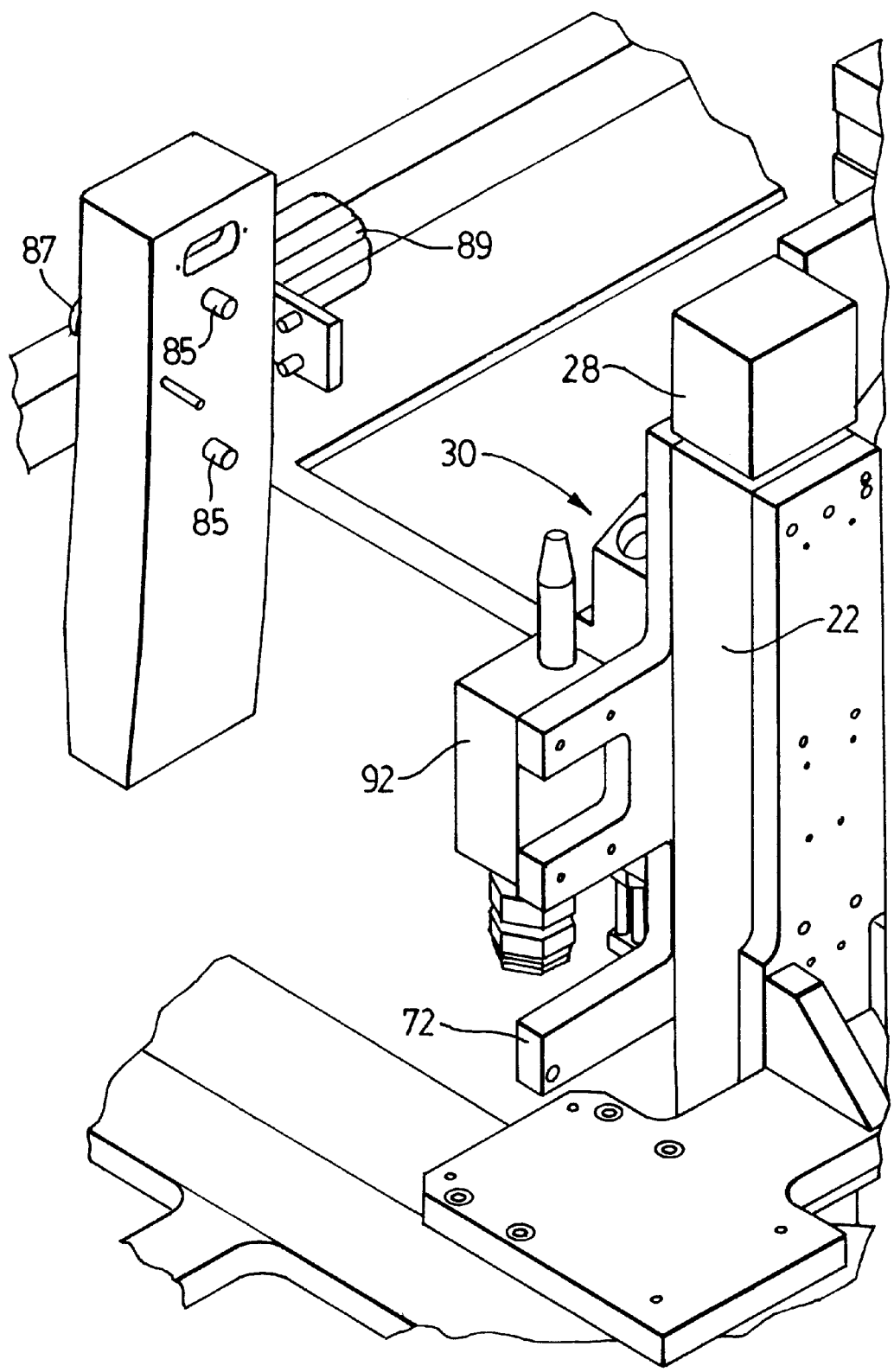
FIG. 9 is an enlarged perspective view of the head assembly showing the pipettor similar to the view shown in FIG. 8 but from behind the head assembly.

Head assembly 30 can have a plurality of tools attached to a Z plate 72, for example a gripper 74, a replicator 76, a picker-head 78 or a pipettor 80. A block 81 is attached to Z plate 72. Block 81, as best seen in FIG. 7, has a plurality of holes 83 therein for receiving positioning pins 85 and attachment screws 87 that are used to position and attach tools to block 81 as best seen in FIG. 9.

Figure 6:
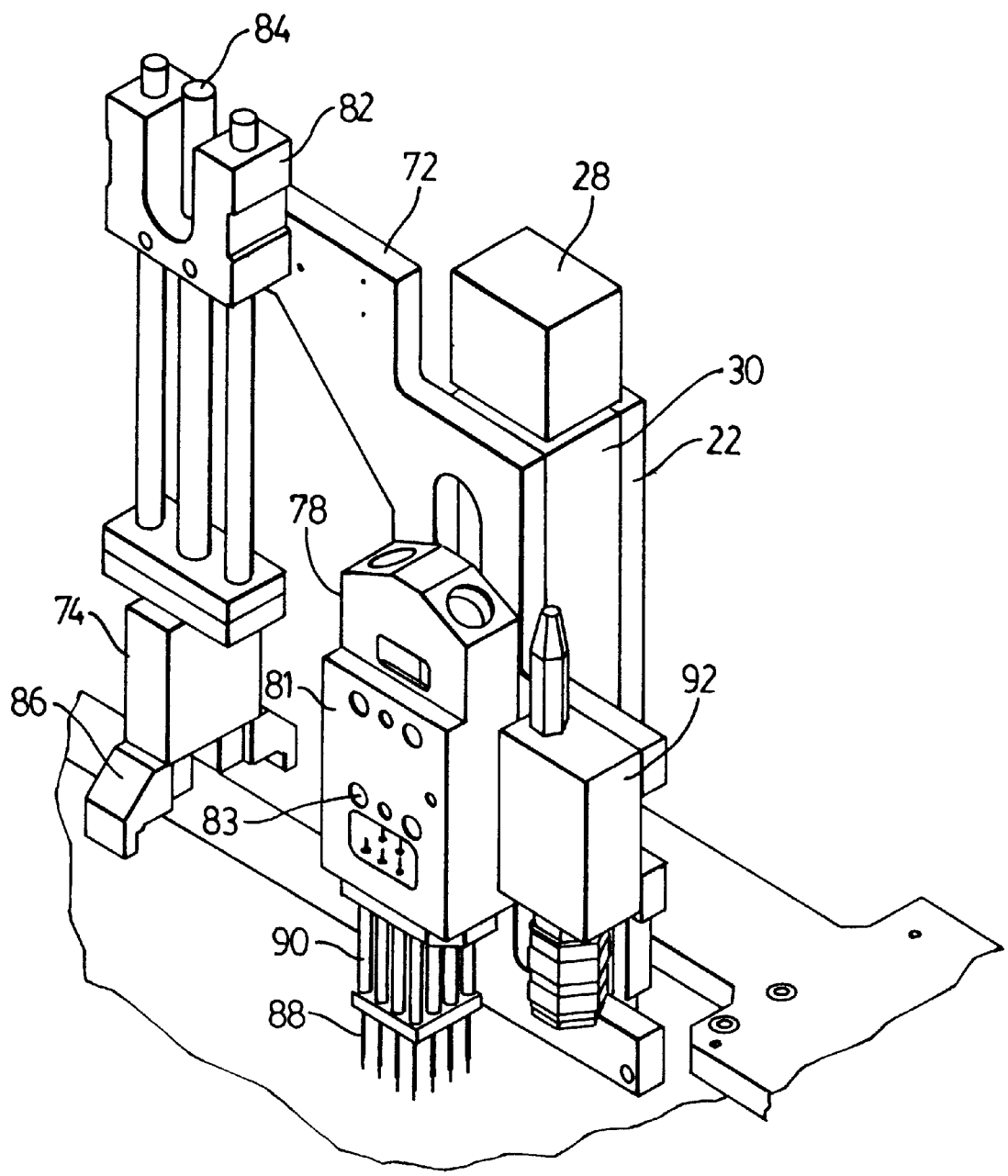
FIG. 6 is an enlarged perspective view of the head assembly of the positioning device of the present invention showing a picker head attached thereto.

Gripper 74 includes a linear guide 82, an actuator 84 and a claw 86, as best seen in FIGS. 1 and 6. The gripper claw 86 is actuated, opened and closed, by means of the actuator 84. The gripper 74 shown herein is adapted to grip microwell plates and all other labware with the same footprint. Gripper 74 would by modified to grip Petri plates 58 and labware of varying foodprints. Gripper 74 is used for automatic gripping and carrying of different labware from one place to another in the working area. For example, a microwell plate 54 can be carried from its position on a platform 46 to a stacker 70.

Figure 10:
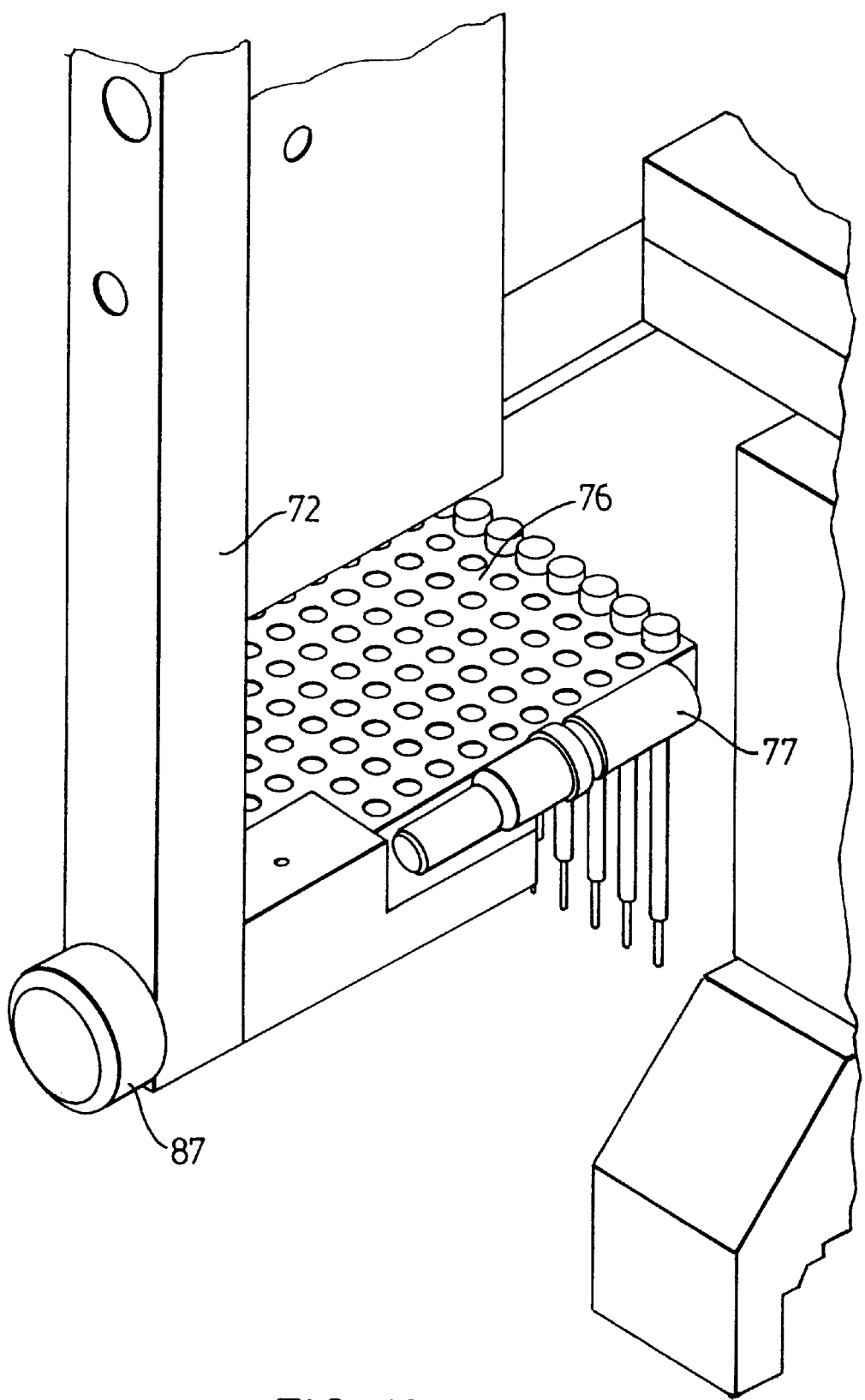
FIG. 10 is an enlarged perspective view of the head assembly of the positioning device of the present invention showing the replicator.

Referring to FIGS. 1 and 10 a replicator 76 is attached to Z-plate 72 with screw 87 and a loading pin 77. Replicator 76 typically has 768, 384 or 96 pins. Replicator 76 is for the simultaneous replication or arraying of 768 samples of bacteria, yeast, or other colonies.

Figure 7:
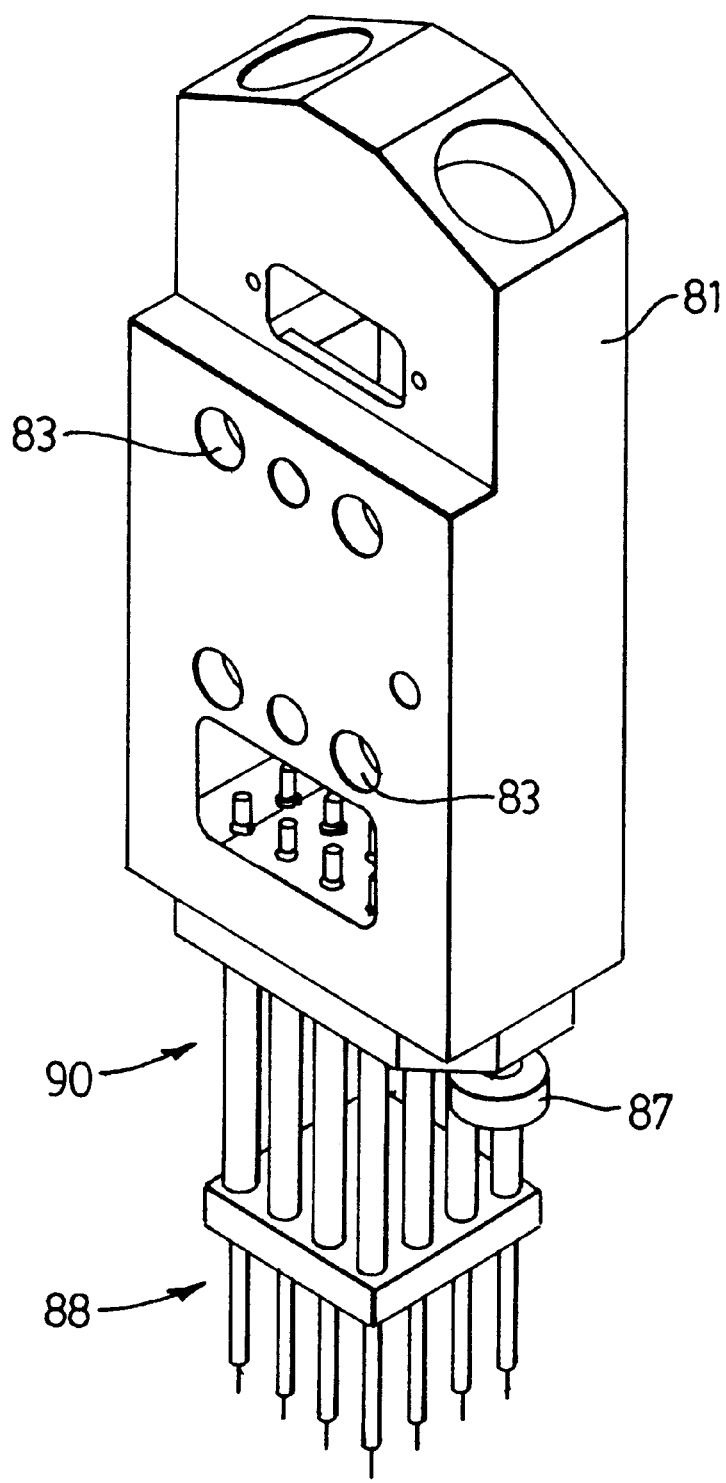
FIG. 7 is a further enlarged perspective view of the picker head of FIG. 6 attached to a block.

Picker-head 78 includes a plurality of pins 88 as best seen in FIG. 6 and FIG. 7. Each pin 88 includes an actuator 90 such that it can be separately actuated. Actuator 90, shown herein, is an air cylinder that moves the pin to the up or down position. In the example shown herein 16 pins are shown. Each pin 88 is used to pick a sample of a randomly distributed bacterium (or other types of) colony from a growth media.

Figure 8:
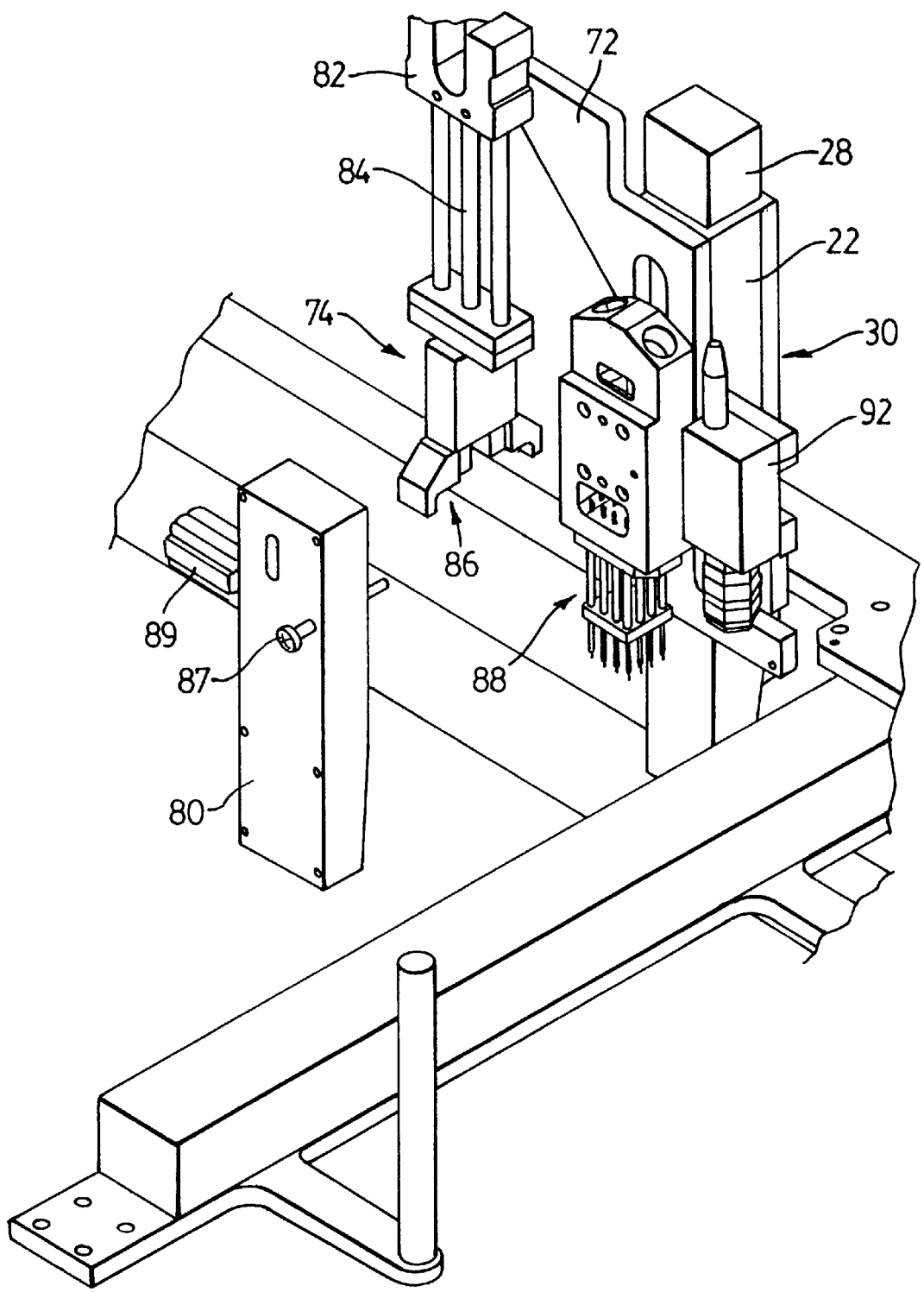
FIG. 8 is an enlarged perspective view of the head assembly of the positioning device of the present invention showing the pipettor.

Pipettor 80 is used for accurate and automatic liquid transferring from one labware to another one as best seen in FIGS. 8 and 9. Pipettor 80 is generally available for manual use and has been adapted to be attached to block 81 and operated by an actuator 89. A wide range of liquid volume can be transferred, e.g., from 0.1 micro-liter to 250 micro-liter or more. A novel design of the pipettor allows for quick attachment or removal. Pipettor 80 can be quickly attached to and detached from block 81 and controlled by the control system. As discussed above the pipettor is attached such that the positioning pins 85 are in registration with corresponding holes 83 in block 81 and a screw 87 attaches it thereto. The actuator 89 is used to automatically release the pipettor tips.

In the embodiment shown herein the gripper 74 and camera 92 are fixed to Z-plate 72 and the replicator 76, picker head 78 and pipettor 80 are attachable to Z-plate 72. The tray loader 94 is attached to connecting plate 42 as described in more detail below.

A CCD (charged coupled device) camera 92 is attached to Z-plate 72. Camera 92 is operably connected to image processing software (not shown). Camera 92 in conjunction with the image processing software is used for the automatic recognition and classification of thousands of bacterium (or other types of) colonies. The X and Y coordinates of the classified colonies are then precisely calculated by the image processing software and sent to robot controller (not shown) for automatic picking of the colonies. In addition camera 92 and image processing software may also be used to take images of yeast or other types of colonies for saving in a central database system for automatic tracking of samples in several stages of the experiments.

A tray loader 94 is attached to connecting plate 42 which connects the X-linear actuator to the parallel rail 40. Tray loader 94 includes a pair of rod supports 96 that extend outwardly from the connecting plate 42 and a pair of rods 98 that extend downwardly from the supports 96. Each rod 98 has a rod actuator 108 that causes the rods 98 to move from a down position to an up position or vice versa. In the down position the rods 98 engage a hole or depression 102 in the trays 16 (as best seen in FIGS. 3 to 5). Tray loaders 94 are used for automatic loading of trays from the elevator unit 14 to one of the platforms 46 and for unloading of trays 16 from platforms 46 to an empty shelf of the elevator unit 14.

Figure 15:
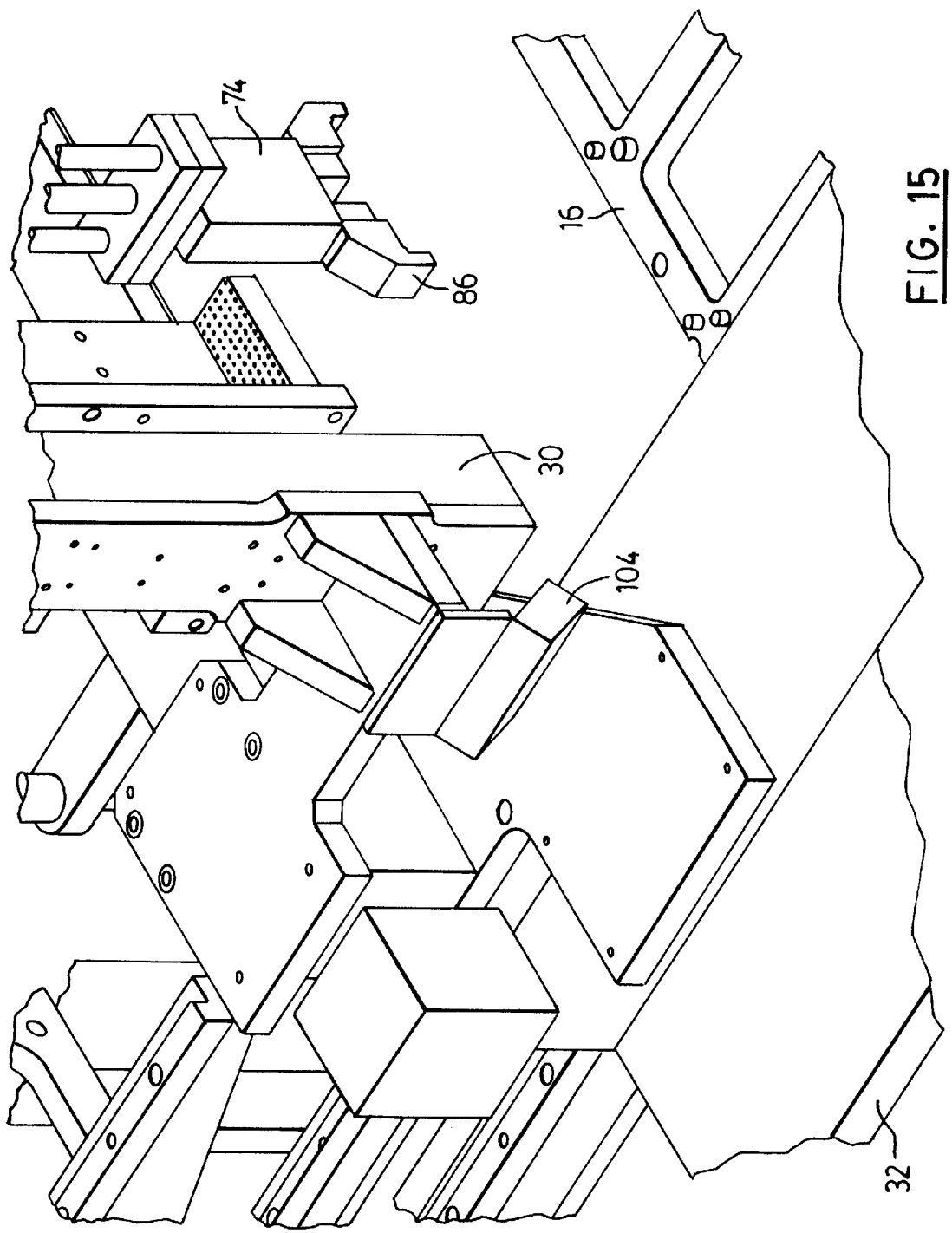
FIG. 15 is an enlarged view of the head assembly including a bar code reader.

A bar code reader 104 shown in FIG. 15 is installed on the machine for automatic reading, verification, and storage of bar code labels on microwell plates or other similar type of labware. Bar code reader 104 is attached to head assembly 30.

Optionally a controlled environment may be included below the elevator unit 14 such that environment for those trays that are not in use and are temporarily stored in the elevator unit may be controlled. The controlled environment would be enclosed and insulated and the temperature and humidity would be controlled. Therefore each time positioning device 10 completes the operations related to the two current trays on the platforms, the trays are loaded to the available bottom shelves of the elevator. Then, the elevator will move the two shelves down into the controlled environment.

Preferably the control system includes intelligent monitoring and data tracking subsystem. These subsystems use information from the artificial vision system and the automatic bar-code scanning system 104. The vision system includes the camera 92 and the image processing software. Together the vision system and the bar-code scanning system 104 can automatically register and verify the current state of the samples each time they are used and processed on the device. The current state of the samples is determined by all relevant information obtained from the user and current and previous images of samples.

Preferably the control system includes flexibility of software such that the user has full control on every task (or function) of the device. Each task (or function) means a specific operation performed by the device, for example, loading a tray from the elevator onto a platform. The tasks are categorized into two categories: 1) micro tasks, which consist of tasks for small and basic operations. Each micro task involves a few motions only, e.g., loading one tray from the elevator onto a platform, or removing the cover of a microwell plate; 2) macro tasks, which consist of tasks with many steps and several micro-tasks, e.g., packing eight microwell plates with their covers. All of the components are operably connected to a graphical user interface (GUI) to facilitate the use and operation of the positioning device 10. The control system together with the GUI allows the user to set up device 10 and then allow the device to run through the operational cycle without being physically monitored.

Following is an example of an operational cycle for the positioning device 10 of the present invention. An operational cycle for picking bacteria colonies may have the following steps:

The user selects the number and types of trays required for the operation. For example, for colony picking the user may select two microwell trays 52 and two Petri plate trays 56.

The user fills the trays 52, 56 with proper labware. In our example, (s)he puts four microwell plates 54 and a large square Petri plate 58 (which holds the bacteria colonies) on each Petri plate tray 56 and puts eight microwell plates 54 on the microwell tray 52 (each microwell tray 52 can hold up to ten microwell plates).

The trays 52, 56 are loaded into elevators shelves 38, with microwell tray 52 are loaded onto alternate shelves 38 and Petri plate trays 56 are loaded onto the free alternate shelves 38 of the elevator unit 14.

The wash stations 64 (FIG. 1) and the sonicator 68 are filled with proper wash solutions.

The required tool for example a Picker Head 78 is attached to Z plate 72.

Using the Graphical User Interface, the user defines all the tasks for this run (in this example, picking-up bacteria colonies from the square Petri plates on Petri plate trays 56 and transferring them to microwell plates 54.

The user runs the program.

The machine automatically performs the following steps:

1. Loads the trays 52, 56 on the shelves 38 and positions the trays onto platforms 46.
2. The camera 92 scans the Petri plate 58 on Petri plate tray 56.
3. The image processing software automatically finds the location of each bacteria colony, and categorizes the bacteria colonies into two groups of good and bad (based on their color, shape, proximity, size, etc.).
4. The picker head 78 picks up good bacteria colonies one by one. For example, a picker head with 16 pins can pick-up 16 colonies (one colony per pin). However, the sixteen colonies are picked up one-by-one in sixteen steps. At each step, one pin 88 moves down (while other 15 pins stay up) to pick up a specific colony.
5. The sixteen picked up samples are transferred to sixteen wells of a microwell plate 54. If the microwell plate has a cover, the gripper 74 (FIG. 1) first removes the cover.
6. The picker pins 88 are washed, sterilized, and dried in the cleaning area (FIG. 2). The wash time and cycle are completely flexible and is determined by the user.
7. Steps 4 to 6 are repeated until all good colonies are picked up from the Petri plate and transferred to microwell plates.
8. The trays 52, 56 on platforms 46 are transferred back to their corresponding shelves.
9. Two new trays 52, 56 on shelves 38 are loaded onto platforms 46.
10. The steps from 2 to 9 are repeated.

It will be appreciated that the above operational cycle is by way of example only and that the user has full flexibility to define any other cycle of tasks.

There are a number of advantages that are realized by the positioning device 10 of the present invention. Positioning device 10 can be used as an automatic colony picking device, which allows the user to pick up thousands of randomly distributed bacteria colonies (or other biological samples) from a growth media (e.g., a gel or agar plate), and transferring the colonies, in a proper order, to another growth media (e.g., a microwell plate). Bacteria colonies grow randomly on a gel plate, with different sizes, varying from 0.1 mm to few millimeters in diameter. Each colony must be first detected and precisely located, using an artificial vision system including the camera 92 and the image processing software. Then the gantry robot 12 moves the head assembly 30 to the colony position and with one of the tools picks up a sample and transfers it to a desired destination (typically a microwell plate 54). All stages of the process are performed automatically under control of a computerized control system.

Positioning device 10 can be used for automatic scanning gel plates, automatic gridding, automatic re-arraying or automatic super positioning. Automatic scanning of gel plates at different stages of a multi-stage biological process, using a high-resolution digital CCD camera 92 includes processing the images of scanned plates using the image processing software and comparing the new images with the images from the previous stages of the biological process. The images and the processed information are then stored into a central database for subsequent retrieval and comparison. Automatic colony arraying includes the picking up an array of colonies (e.g., 768 colonies) simultaneously, and transferring all samples to a new gel plate, a microwell plate 52 or another growth media. Automatic gridding includes picking up an array or an individual biological samples and spotting them (it) on a membrane 62. Automatic re-arraying includes picking up selected individual colonies, and re-positioning them in a pre-defined order. Automatic super positioning includes positioning one or more biological samples on one or more other biological samples for mating or other biological interactions.

Positioning device 10 can automatically change it's own configuration to perform variety of functions without any human intervention. The configuration of the positioning device 10 is changed by loading and unloading different trays 16 form the elevator unit 14 and transferring plates for the trays to the stacking area 50. Further, positioning device 10 can automatically pack and unpack different labware (e.g., microwell plates 54), into (and from) reusable stackers 70.

Positioning device 10 provides for intelligent monitoring and data tracking which is based on the machine vision system (including the camera 92) and an automatic bar-code scanning system (including the bar code reader 104). Each plate is identified with a unique bar-code number, which is read automatically during the run, and compared with the stored information in the central database to avoid any possible mistake.

Positioning device 10 includes a packing/unpacking system that allows for automatic packing or unpacking of several microwell plates (or other similar labware) into or from reusable packages. Each package is used to transfer and process multiple plates (one batch of plates may contain eight or more plates) simultaneously. Each package or batch is labeled and identified by a bar-code label. Such an identification number allows for systematic storing, tracking, and retrieval of all the information related to that batch.

It will be appreciated that the above description related to the invention by way of example only. Many variations on the invention will be obvious to those skilled in the art and such obvious variations are within the scope of the invention as described herein whether or not expressly described.

What is claimed as the invention is:

1. A positioning device comprising:
    a head assembly;
    a work-space spaced below the head assembly for receiving at least one tray;
    an X moving means for moving the head assembly in the X direction;
    a Y moving means for moving the head assembly in the Y direction;
    a Z moving means for moving the head assembly in the Z direction;
    a scanning means for scanning the work-space;
    an elevator unit having a plurality of shelves arranged in a series one above another each shelf adapted to receive at least one tray, the shelves being movable in the Z direction;

a tray moving means for moving a tray between the elevator unit and the work-space; and a control system operably connected to the head assembly, X moving means, Y moving means, Z moving means, scanning means, elevator unit and tray moving means for controlling the movement of the head assembly in the X, Y and Z direction, for controlling the movement of the shelves in the Z direction and for controlling the tray moving means.

2. A positioning device as claimed in claim 1 wherein the X moving means includes an X linear actuator and an X motor and the Y moving means includes a Y linear actuator and a Y motor and the X linear actuator and the Y linear actuator define the work-space.

3. A positioning device as claimed in claim 2 wherein the elevator unit is positioned adjacent to the work-space.

4. A positioning device as claimed in claim 3 wherein the tray moving means includes a movable pair of rods attached to and spaced from the Y linear actuator in the direction of the elevator unit, movable upwardly and downwardly and moveable in the X direction by the X linear actuator and the rods are adapted to engage a tray.

5. A positioning device as claimed in claim 4 wherein the elevator unit includes a refrigerator enclosure.

6. A positioning device as claimed in claim 5 further including pairs of stoppers attached to side portions of the shelves remote from the work-space adapted to position the tray positioned on the shelve closer to the work-space than the tray positioned on a shelf without a stopper.

7. A positioning device as claimed in claim 6 further including a plurality of pairs of stoppers and wherein the stoppers are arranged such that trays positioned on lower shelves are closer to the work-space as compared to trays positioned on higher shelves.

8. A positioning device as claimed in claim 7 wherein each shelf in the elevator unit includes two spaced apart side portions each having a ledge extending inwardly and a tray is received thereon.

9. A positioning device as claimed in claim 5 wherein the tray moving means further includes an elevator X linear actuator for moving a tray towards the rods.

10. A positioning device as claimed in claim 1 wherein the tray is chosen from a group including a microwell tray having a plurality of microwell plates, a Petri plate tray having at least one Petri plate and a membrane holder tray having at least one membrane.

11. A positioning device as claimed in claim 1 further including a stacking area having a plurality of stackers.

12. A positioning device as claimed in claim 1 further including a cleaning area wherein the elements of the cleaning area are chosen from a group including a washing station, a drying station and a sonicator.

13. A positioning device as claimed in claim 1 wherein the head assembly has at least one tool attached thereto, the tool being operably attached to the control system and the tool being chosen from a group consisting of a gripper, a replicator, a picker head, a pipettor, a bar code reader and a camera.

14. A positioning device as claimed in claim 13 wherein the head assembly has a plurality of tools attached there to and one of the tools is a camera.

15. A positioning device as claimed in claim 14 wherein the camera is operably connected to a data tracking means.

16. A positioning device as claimed in claim 15 wherein the bar code reader is one of the tools attached to the head assembly and the bar code reader is operably connected to the data tracking means.

17. A positioning device as claimed in claim 13 wherein the head assembly has at least three tools attached thereto including a gripper and a camera.

18. A positioning device as claimed in claim 13 wherein the gripper is adapted to grip labware.

19. A positioning device as claimed in claim 18 wherein the labware are chosen from a group consisting of a microwell plate, a Petri plate and a membrane.

* * * * *